United States Patent [19]

Plattner

[11] 4,092,349

[45] May 30, 1978

[54] 11-DESOXY-15-THIAPROSTAGLANDINS

[75] Inventor: Jacob J. Plattner, East Lyme, Conn.

[73] Assignee: Pfizer Inc., New York, N.Y.

[21] Appl. No.: 740,381

[22] Filed: Nov. 10, 1976

[51] Int. Cl.$^2$ .................... C07C 149/40; A61K 31/19

[52] U.S. Cl. ........................................ 260/516; 560/9;
260/308 D; 260/343.3 P; 260/346.22; 260/948;
542/429; 424/309; 260/558 S

[58] Field of Search ..................... 260/470, 516; 560/9

[56] References Cited

U.S. PATENT DOCUMENTS

| | | | |
|---|---|---|---|
| 3,932,487 | 1/1976 | Kramer et al. .................. | 260/516 |
| 4,024,179 | 5/1977 | Bindra .............................. | 260/473 A |

OTHER PUBLICATIONS

Plattner, Tetrahedrin Letters, No. 19, pp. 1629–1632 (1977).

*Primary Examiner*—James O. Thomas, Jr.
*Assistant Examiner*—Michael Shippen
*Attorney, Agent, or Firm*—Connolly and Hutz

[57] ABSTRACT

11-Desoxy-15-thia-16-aryl-$\omega$-tetranor prostanoid compounds having a carboxyl, tetrazole, or substituted imide at $C_1$, having prostaglandin-like anti-ulcer activity and their synthesis from the 11-desoxy "Corey Lactone".

4 Claims, No Drawings

11-DESOXY-15-THIAPROSTAGLANDINS

BACKGROUND OF THE INVENTION

This invention relates to a novel series of 11-desoxy-15-thia-16-aryl-ω-tetranor prostaglandin compounds which have specific prostaglandin-like biological activity, the processes for making such compounds and synthetic intermediates employed in these processes.

The $C_{20}$ unsaturated fatty acids, known as prostaglandins, form a large family of naturally-occurring compounds. These molecules may have as many as five asymmetric centers and are present in and evoke response from a diversity of biological tissues. An example of a particular species of the prostaglandin E genera is $PGE_2$ pictured below.

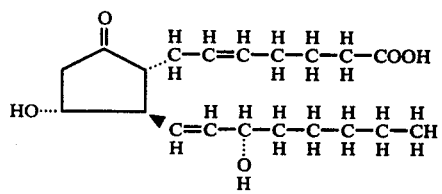

According to the notation usually employed to describe the stereochemistry of prostaglandins, a heavy solid line represents the β configuration. In a like manner, a dotted or hashed line represents the α configuration. Thus, the configuration of natural prostaglandin $E_2$, pictured above, is α at carbon atoms 8, 11 and 15, and β at carbon atoms 12 [S. Bergstrom, et al., Acta. Chem. Scand., 16, 601 (1962)].

By the same terminology, a wavy line represents a mixture of the two forms α and β. Thus, $PGE_1$ having the structure:

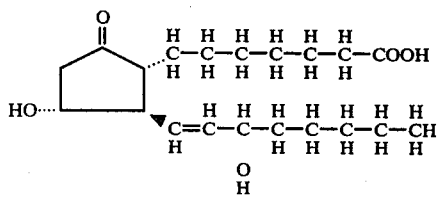

represents a mixture of the epimers

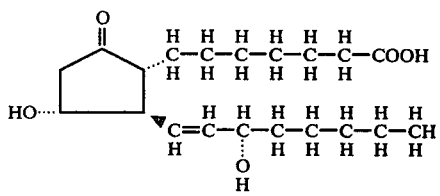

and

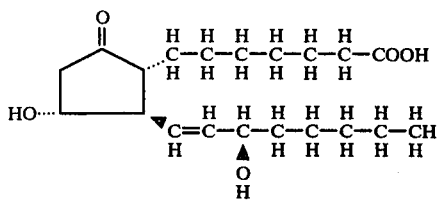

Three nomenclature systems are used to describe various cogeners of prostaglandins. The first is a trivial system based upon the terms PGE, PGF and PGA. In this system, a compound of the present invention having the structure

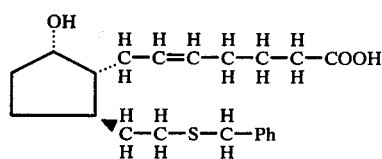

would have the same 11-desoxy-13,14-dihydro-14-(benzylthio)-ω-hexanor $PGF_{2α}$.

The second system is based upon prostanoic acid which has the structure and position numbering:

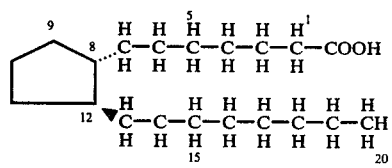

In this nomenclature system, a compound of the present invention which has the structure

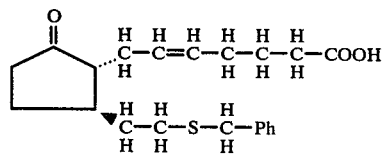

would have the name 9-oxo-14-(benzylthio)-cis-5-ω-hexanorprostenoic acid.

The third form is the preferred, systematic nomenclature system. In this system, the compound immediately above is called 7-[5-oxo-2β-(benzylthioethylenyl)cyclopent-1α-yl]hept-cis-5-enoic acid.

The prostaglandins have several centers of asymmetry, and can exist in the racemic (optically inactive) form and in either of the two enantiomeric (optically active) forms, i.e., the dextrorotatory (D) and levorotatory (L) forms. As drawn above, each prostaglandin structure represents the particular optically active form or enantiomer which is analogous to or the same as the naturally occurring or "nat" prostaglandin. The mirror image or optical antipode of each of the above structures represents the other enantiomer of that compound and is termed the "ent" prostaglandin.

For instance, the optical antipode of 7-[5-oxo-2β-(3α-hydroxyoct-trans-1-enyl)cyclopent-1α-yl]heptanoic acid is drawn as:

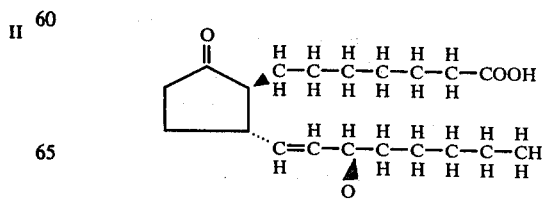

and is called 7-[5-oxo-2α-(3β-hydroxyoct-trans-1-enyl)-cyclopent-1β-yl]-heptanoic acid or "ent" 11-desoxy PGE$_1$.

It is a fact that chemical experimentation on either member of an enantiomeric pair or upon a mixture of the two will produce the same and identical results.

The natural prostaglandins and many of their derivatives such as the esters, acylates, and pharmacologically acceptable salts, are extremely potent inducers of various biological responses [D. E. Wilson, Arch. Intern. Med., 133 (29) 1974)] in tissues composed of smooth muscle such as those of the cardiovascular, pulmonary, gastrointestinal and reproductive systems; in cellular tissues such as those of the central nervous, hematologic, reproductive, gastrointestinal, pulmonary, nephritic, epidermal, cardiovascular and adipose systems and also operate as mediators in the process of homeostasis. With such a wide range of responses, it is apparent that the prostaglandins are involved in basic biological processes of the cell. Indeed, this basic implication of prostaglandins is supported by the fact that they can be found in cellular tissue of all mammals and numerous other animals.

Often on such a cellular level the actions of closely related natural prostaglandins may be opposite. For instance, the effect of PGE$_2$ on human platelets is enhancement of aggregation while that of PGE$_1$ is inhibition of aggregation.

Such contrasting effects may also be observed at the tissue level. For instance, in vivo PGE$_2$ action on the cardiovascular system of mammals manifests itself by causing hypotension while the in vivo action of PGF$_{2\alpha}$ is hypertension [J. B. Lee, Arch. Intern. Med., 133 56 (1974)]. However, at present it is difficult to predict a specific biological action of a group of structurally related prostaglandins by considering the relationship between it and another group of prostaglandins whose pharmacology is known. For instance, while the cardiovascular actions of PGE$_2$ and PGF$_{2\alpha}$ are opposite as described above, their in vivo and in vitro action on mammalian uterine smooth muscle is the same and is stimulatory (causes contraction) [H. R. Behrman, et. al., Arch. Intern. Med., 133 77 (1974)].

In the preparation of synthetic pharmaceutical agents, among the principal objects is the development of compounds which are highly selective in their pharmacological activity and which have an increased duration of activity over their naturally occurring relatives. In a series of compounds similar to the naturally-occurring prostaglandins, increasing selectivity of a single compound usually involves the enhancement of one prostaglandin-like physiological effect and the diminution of the others. The potential benefits of this selectivity are manifold, for example, a decrease in the severe side effects such as diarrhea and emesis which are frequently observed following administration of the natural prostaglandins. A divorce of cardiovascular and bronchodilator activity which are both embraced by natural prostaglandins also would have obvious medicinal potential. Recent developments directed toward an increase of biological selectivity include the 11-desoxy prostaglandins [N. H. Anderson, Arch. Intern. Med., 133, 30 (1974) Review ] 2-descarboxy-2-(tetrazol-5-yl)-11-desoxy-15-substituted —pentanorprostaglandins (M. R. Johnson et al., U.S. Pat. No. 3,932,389) where certain modifications are cited as producing selective vasodilator, antiulcer, antifertility, bronchodilator and antihypertensive properties and N-acyl or N-sulfonyl prostaglandin carboxamides (U.S. Pat. No. 3,954,741).

However, present in all of these synthetic prostaglandin pharmaceutical agents is the C15 hydroxyl group. It has long been known that one of the primary routes of metabolism and deactivation of prostaglandins is enzymatic oxidation of the C15 hydroxyl group to a C15 keto group. [T. O. Oesterling, et al., J. Pharm. Sci., 61, 1861 (1972)]. The product of this enzymatic transformation is not characterized by the breadth of physiological effects of natural prostaglandins and illustrates the importance of the C15 hydroxyl for prostaglandin biological activity [N. H. Anderson, et al., Arch. Intern. Med., 133, 30 (1974)]. This importance is also aptly demonstrated by the attenuation of biological activity when the C11 and C15 hydroxyls are completely removed. In a biological test, gastric acid secretion, which has direct relation to the biological activity of the compounds of the present invention, 11,15-bisdesoxy-13,14-dihydro-ω-trisnor PGE$_1$ had significantly less activity than PGE$_1$ [J. F. Poletto, et al., J. Med. Chem., 18, 359 (1975)]. Thus, it has surprisingly been discovered that the compounds of the present invention, which have neither the C11 nor C15 hydroxyl groups so essential for prostaglandin biological activity, have potent and selective prostaglandin-like biological activity.

SUMMARY OF THE INVENTION

The compounds of the present invention are prostaglandin derivatives having potent and selective antiulcer biological activity. These compounds have the formula:

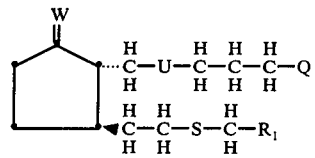

and the enantiomer and racemate thereof, wherein:
Q is selected from the group consisting of —COOR$_2$, tetrazol-5-yl and —CONHCOR$_3$;
U is ethylene or cis-vinylene;

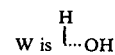

or oxygen;
R$_1$ is selected from the group consisting of phenyl and monosubstituted phenyl, said substituent being selected from the group consisting of fluoro, chloro, methyl, methoxy and trifluoromethyl;
R$_2$ is selected from the group consisting of hydrogen, alkyl having from one to four carbons;
R$_3$ is selected from the group consisting of alkyl having from one to four carbons and phenyl;
and the pharmaceutically acceptable alkali, alkaline earth and ammonium salts of the compounds having a carboxy or a tetrazol-5-yl group.

In addition, the present invention comprises intermediates for the synthesis of the final products of the invention. One of these novel intermediates has the structure:

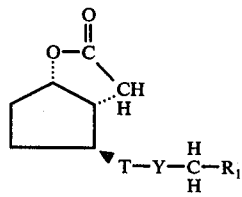

and the epimers thereof,
wherein:
Y is —S— or —SO—;
T is ethylene, or vinylene, provided that when Y is —SO—, T is vinylene;
and $R_1$ is selected from the group consisting of phenyl and monosubstituted phenyl, said substituent being selected from the group consisting of fluoro, chloro, methyl, methoxy and trifluoromethyl.

The other novel intermediate has the structure:

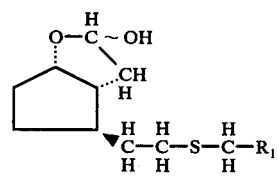

and the epimers thereof,
wherein:
$R_1$ is defined above.

Preferred for their anti-ulcer activity are the compounds of the present invention having the structures:

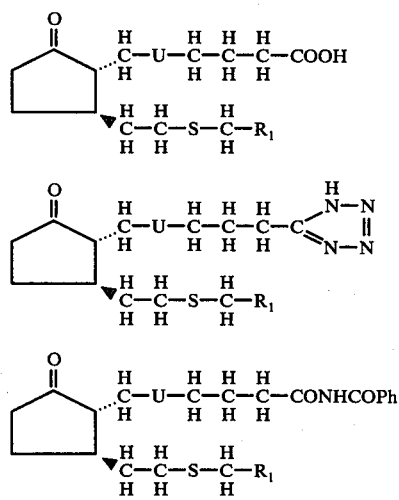

and the enantiomers and racemates thereof, wherein U and $R_1$ are defined as above.

Especially preferred for the above stated purpose are:

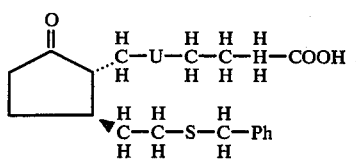

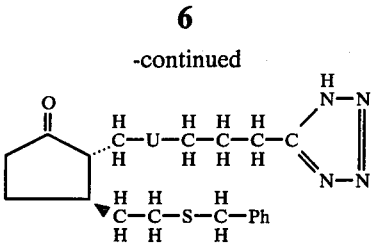

The 11-desoxy-13,14-dihydro-14-benzylthio-ω-hexanor $PGE_2$ compounds being the most preferred for their anti-ulcer activity are: 7-[5-oxo-2β-(benzylthioethylenyl)cyclopent-1α-yl]hept-5-enoic acid and 2β-benzylthioethylenyl-1α-[6-(tetrazol-5-yl)hex-cis-2-enyl]cyclopentan-5-one.

DETAILED DESCRIPTION OF THE INVENTION

The prostaglandins of the instant invention are formed by a multi-step synthetic sequence which allows the attachment of the α- and ω-(top and bottom) side chains to the known optically active substrate 1-[2β-formyl-5α-hydroxycyclopent-1α-yl]acetic acid, γ-lactone, 1 [E. J. Corey and B. B. Snider, J. Org. Chem., 39, 256 (1974)] and allows the performance of various modifications upon the thus formed 9-hydroxy-cis-5-prostenoid intermediate. Schemes A, B, C and D illustrate that sequence and depict the methods by which the synthesis is accomplished.

The overview of the Schemes is described as follows. Scheme A shows the attachment of the ω-chain to the cyclopentyl ring. Scheme B shows the attachment of the α-chain to the product of Scheme A, thus preparing 9α-hydroxy-cis-5-prostenoic acid and tetrazol products. Scheme C shows the modifications of the 9α-hydroxy-cis-5-prostenoic acids and tetrazoles to produce the 9-oxo and 9-hydroxy prostanoid and cis-5-prostenoid compounds of the present invention. Scheme D shows the modification of the prostenoic and prostanoic acids into esters and imides.

The use of natural configuration γ-lactone of formula 1 allows the preparation of the prostaglandin compounds of the instant invention having the natural configuration at positions C8, C9 and C12.

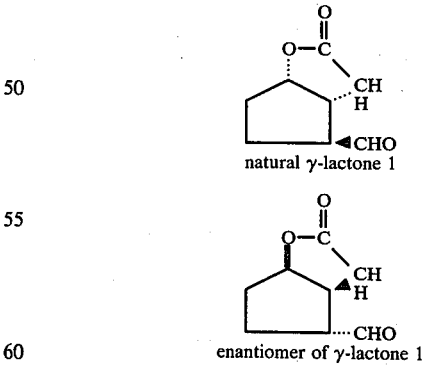

natural γ-lactone 1 enantiomer of γ-lactone 1

If it is desired to synthesize the enantiomer or the racemate of the natural configuration compounds of the present invention, then it is necessary only to start with the enantiomer or racemate of γ-lactone 1. Although only the natural configuration compounds are shown, it shall be hereafter known that the compounds of the present invention, their synthesis and the methods thereof encompass both enantiomers and the racemate.

Scheme A
ω-chain attachment

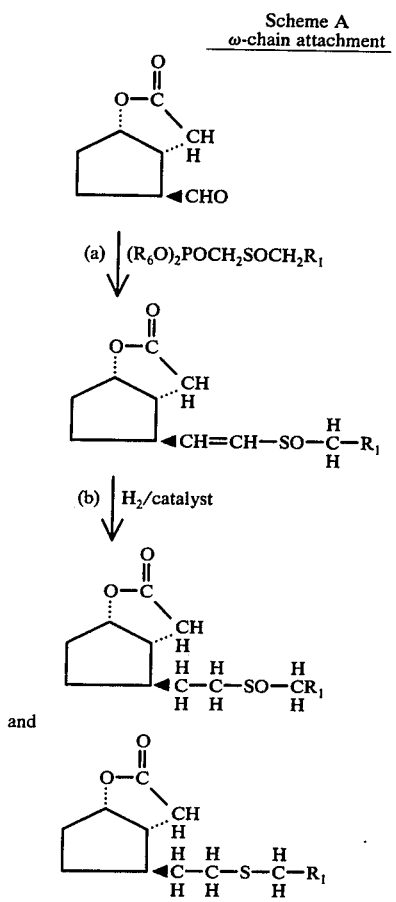

R₁ is as defined above
R₆ is as defined below

The synthetic design presented in Scheme A illustrates the method, reactions (a) and (b), by which 2-[2β-(arylmethylthioethylenyl)-5α-hydroxycyclopent-1α-yl]acetic acid, γ-lactone and the corresponding 2β-arylmethylsulfinylethylenyl compound are created. Although the γ-lactone starting material of formula 1, which is used in reaction (a), is known [E. J. Corey, opt. cit.], the phosphonate starting material having the structure

wherein $R_1$ is defined as above and $R_6$ is alkyl having from one to three carbon atoms, is novel. The preparation of the above phosphonate is accomplished in two steps, the first of which is an Arbuzov reaction of trialkyl phosphite having one to three carbon atoms with arylmethyl halomethyl sulfide which is prepared according to the method of Bohme, Fischer and Frank [Ann., 563, 54 (1949)]. The second reaction is the oxidation of the sulfide moiety to a sulfoxide moiety. Both of these reactions are illustrated as follows:

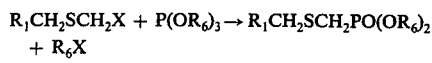

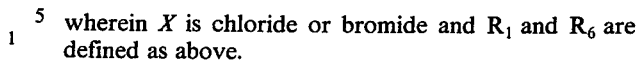

wherein $X$ is chloride or bromide and $R_1$ and $R_6$ are defined as above.

The usual procedure of the first reaction consists of contacting the sulfide and trialkyl phosphite neat while heating at temperatures of from 120° to 165° C. or just below the boiling point of the trialkyl phosphite and removing the forming, volatile alkyl halide ($R_6X$). After all alkyl halide has been removed, the temperature can be raised to above the boiling point of the trialkyl phosphite in order to guarantee the completion of the reaction. To those skilled in the art, it will be apparent when the reaction is complete and this can be tested by chromatographing a small aliquot of the reaction material on a thin layer chromatography (TLC) plate, usually silica gel on glass, and comparing the developed TLC of the reaction material to that of the staring material. [Such methods are discussed in J. M. Bobbitt et al. "Introduction to Chromatography", Van Nostrand-Reinhold N.Y. 1968]. The isolation of the desired product from the reaction mixture is capably handled by the common techniques of vacuum distillation, column chromatograph or extraction.

The sulfide is then oxidized to the sulfoxide according to the second reaction. Any method which is capable of selectively oxidizing sulfides to sulfoxides can be employed in this case to produce the desired phosphonate. Some of these methods which are known to those skilled in the art include oxidation with hydrogen peroxide and oxidation with perorganic acids, especially m-chloroperbenzoic acid. If the preferred oxidizing agent is selected, contact of one equivalent of it with the purified sulfide in an inert solvent such as methylene chloride or chloroform at about the temperature of an ice bath to ambient will allow easy preparation of the desired phosphonate. In general, this reaction is complete within two hours but longer times may be necessary depending upon a reaction monitor assay test such as an infrared spectrum, nuclear magnetic spectrum or TLC (see above).

Upon achieving the preparation of the desired phosphonate, the synthesis of 2-[2β-(arylmethylsulfinyl-vinylenyl)-5α-hydroxy-cyclopent-1α-yl]acetic acid, γ-lactone of formula A can begin. The ω-chain attachment procedure, which is step (a) of Scheme A, is usually conducted by first contacting the above synthesized phosphonate with an equivalent of base such as sodium hydride or n-butyl lithium in an inert ethereal solvent such as ether, tetrahydrofuran or dimethoxyethane at −10° C. to 30° C. or preferably the temperature of an ice bath, and stirring until all the base is gone, usually 1 hour. The thus formed sodium or lithium phosphonate salt is then contacted with a solution of an equivalent of γ-lactone aldehyde 1 and the same inert solvent at temperatures of an ice bath to solvent reflux and usually at ambient temperature. The course of this Horner-Wittig reaction can be followed by the usual reaction monitor techniques of nuclear magnetic resonance spectroscopy, infrared spectroscopy and thin layer chromatography. The preferred method is thin layer chromatography of the reaction mixture against the starting γ-lactone aldehyde 1 on silica gel using benzene/ether as an eluant. After it is determined by such method that the reaction is essentially complete, the course of which is usually overnight (18 hours), the reaction mixture is quenched with a weak organic acid such as acetic acid and product is isolated.

There exist four geometric isomers of the product from this Horner-Wittig type olefin formation. They are the cis and trans isomers of the double bond and the R and S isomers of the sulfoxide group. Because of their differing polarities they can be separated to a substantial extent by such familiar methods as of column chromatography and high pressure liquid chromatography. For the purposes of the present invention, however, the isomers are equivalent and are used as a mixture in the subsequent reduction step.

The reduction step (b) Scheme A, of the sulfoxide-γ-lactone, A, is usually accomplished by catalytic methods. Any procedure which will bring sulfoxide-γ-lactone A into contact with hydrogen over a noble metal catalyst will be effective for the desired reduction. The preferred method consists of agitating a solution of the sulfoxide-γ-lactone A in a polar solvent such as methanol, ethanol or propanol and, if desired, a small amount of a weak organic acid such as acetic or propionic acid together with a noble metal catalyst in 1 to 4 atmospheres of hydrogen. The usual catalysts include palladium on carbon and platinum oxide. Convenient temperatures include from 10° C. to that just below refluxing solvent and preferably ambient temperature. The reaction is usually monitored by absorption of hydrogen which when completely ceased will usually signal the end of the reaction. Because of the sulfide nature of one of the products, it is often necessary to add fresh catalyst during the course of the reaction in order to complete hydrogenation.

The hydrogenation reaction produces two products, γ-lactones B and C, which are easily separable by the usual methods of column chromatography. The sulfide γ-lactone C is then converted into the final products of the invention according to the steps presented in Schemes B and C.

An alternative method for preparation of the sulfide γ-lactone C which avoids the intermediacy of the sulfoxide is shown below.

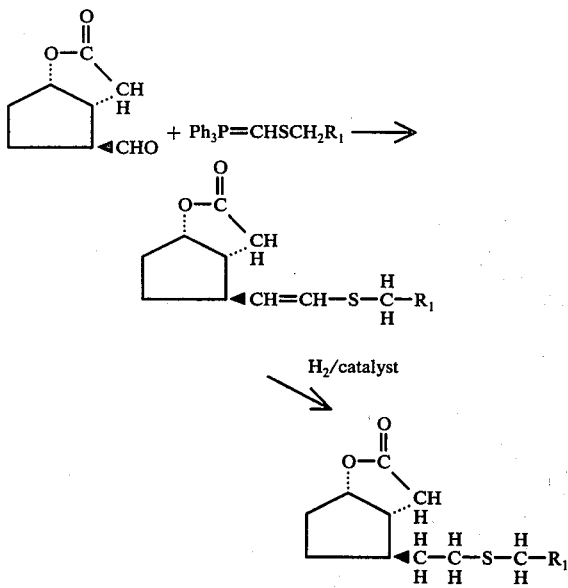

The first reaction is a Wittig reaction of γ-lactone aldehyde, 1, with a phosphorane of the structure $$Ph_3P=CHSCH_2R_1$$

wherein $R_1$ is defined as above. The conditions of this reaction are the same as those of step (a) Scheme A and the phosphorane is generated from the phosphonium chloride or bromide having the structure $$Ph_{3+}PCH_2SCH_2R_1 \; Br^- \text{ or } Cl^-$$

by contact with a base such as sodium hydride or n-butyl lithium in the same manner as that of step (a).

The second reaction is the catalytic hydrogenation of the double bond which is conducted under the same conditions as step (b) Scheme A.

The preparation of the above phosphonium salt can conveniently be accomplished by contacting a slight excess (ca. 1.1 equivalents) of triphenyl phosphine with the above arylmethyl halomethyl sulfide ($R_1CH_2SCH_2X$), wherein $R_1$ and X are as previously defined, in an inert solvent such as benzene, ether, tetrahydrofuran or dimethoxyethane at temperatures from that of an ice bath to refluxing solvent until the reaction is essentially complete, usually 4 to 20 hours.

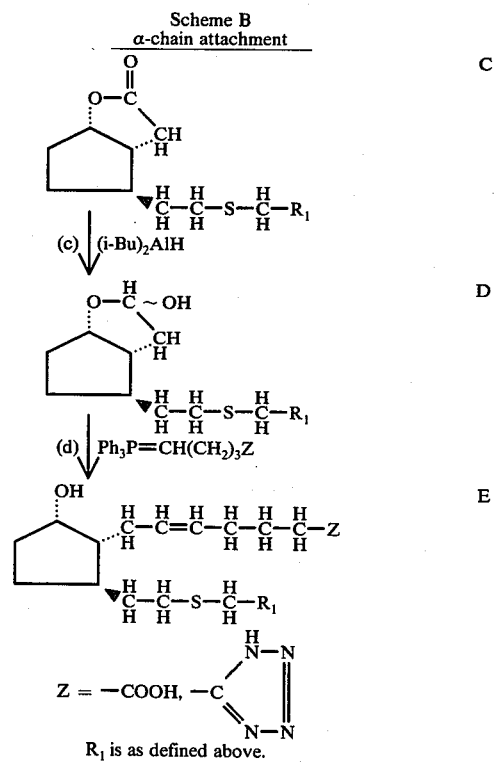

$R_1$ is as defined above.

The reactions presented in Scheme B illustrate the sequence by which the α or top side chain is attached to 2-[2β-(arylmethylthioethylenyl)-5α-hydroxycyclopent-1α-yl]acetic acid, γ-lactone of formula C. Briefly, reaction (c) is the reduction of the γ-lactone moiety of compound C to produce the γ-hemiacetal moiety of compound D. Any reagent capable of causing the reduction of only the lactone moiety to a hemiacetal moiety will suffice. It will be most convenient to employ the selective reducing agent diisobutylaluminum hydride. Reaction (d) is the Wittig reaction of the γ-hemiacetal compound D with the sodium or lithium salt of 4-(tetrazol-5-yl)butyltriphenylphosphorane or 4-(carboxy)butyltriphenylphosphorane to produce a compound of the present invention, that of formula E.

The methods, conditions and procedures of the reactions (c) and (d), presented in Scheme B, are known to those familiar with the prostaglandin art as are the reagents. For instance, the methods for the reduction, step (c), and the Wittig reaction, step (d), when Z of the phosphorane, $Ph_3P=CH(CH_2)_3Z$, is $CO_2H$, are described by E. J. Corey et al., J. Amer. Chem. Soc. 93, 1491 (1971) and also in U.S. 3,956,284. The analogous methods for use with the phosphorane, $Ph_3P=CH(CH_2)_3Z$, having Z as a tetrazol-5-yl are described in U.S. Pat. Nos. 3,928,391 and 3,883,513. Examples describing the use of both types of phosphorane as reactants with the γ-hemiacetal compound of formula D as well as the preparation of γ-hemiacetal compound D are presented below as enabling art.

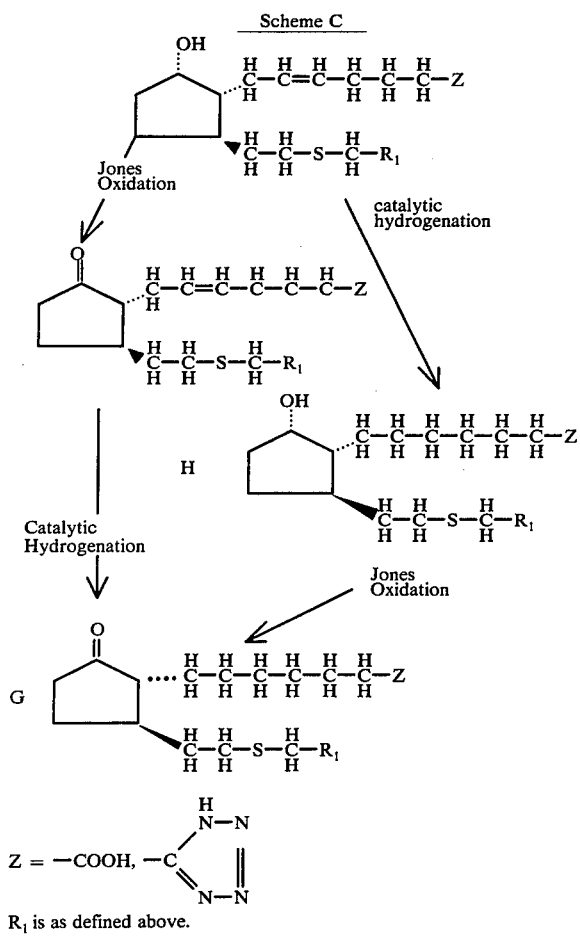

$R_1$ is as defined above.

The sequence presented in Scheme C illustrates the methods by which the prostenoic compound of formula E is modified into several of the other compounds of the instant invention having the formulas F, G and H. According to what modification is desired, these compounds are synthesized by either or both of two types of reactions; a "Jones" or analogous oxidation and a catalytic hydrogenation over a noble metal catalyst. The prostenoic compound F is prepared from compound E by a Jones oxidation. Compound H is prepared from E by a catalytic hydrogenation. Compound G is prepared from F by a catalytic hydrogenation or from H by a Jones oxidation. Briefly, the oxidation procedure allows contact of the alcohol E or H with Jones Reagent or other similar oxidizing reagent for a short time in an inert organic solvent at −10° to 20° and the catalytic hydrogenation procedure is the same as that described supra, step (b) Scheme A.

The methods, conditions and procedures for both of these two reactions as applied to the chemistry of prostaglandins are known to those familiar with the art. [cf. Corey, opt. cit., U.S. Pat. Nos. 3,883,513 and 3,956,284]. The examples given below provide enabling art.

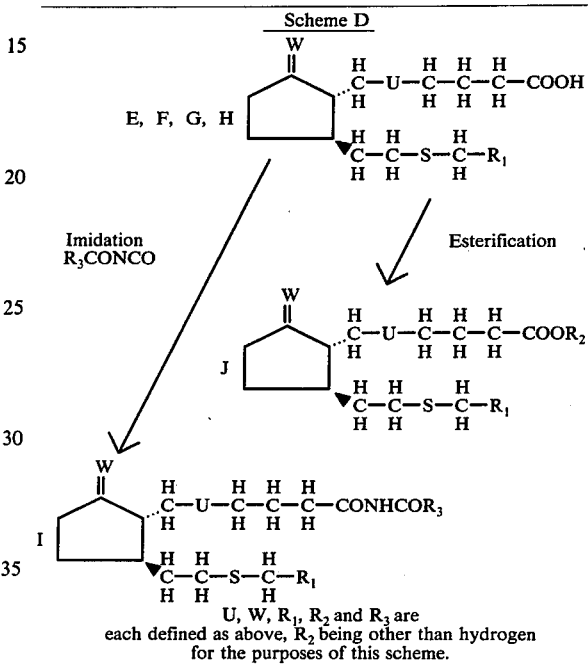

$U$, $W$, $R_1$, $R_2$ and $R_3$ are each defined as above, $R_2$ being other than hydrogen for the purposes of this scheme.

The sequence presented in Scheme D illustrates the preparation of prostenoic and prostanoic imides and esters from the compounds of formulas E, F, G and H wherein Z is a carboxylic acid. Esterification of any of the carboxylic acids of formulas E, F, G or H can be achieved by several common techniques including Fischer esterification, and use of diazoalkane compounds of appropriate structure. Imidation can be achieved by contacting the carboxylic acids with an acyl isocyanate of appropriate structure. The following descriptions provide the usual conditions for all of these methods.

The usual Fischer esterification technique consists of dissolving a carboxylic acid of formula E, F, G or H in a dry alkanol solvent having one to four carbon atoms, adding a catalytic amount of mineral or organic acid such as sulfuric acid or p-toluene sulfonic acid and allowing the reaction to proceed at ambient to solvent reflux temperature for 8 hours to two days. Alternatively, the alcohol solvent can be saturated with hydrogen chloride and then the carboxylic acid compound E, F, G or H can be added to this acidic solution at ambient temperature. The resultant esterification reaction can be allowed to proceed at ambient temperature usually overnight. The product esters, J, wherein $R_2$ is alkyl, formed in both of the above manners can be isolated by neutralization of the strong acid catalyst, removal of solvent and purification by extraction or column chromatography techniques.

Esterification by reaction of the carboxylic acid compound E, F, G or H with n-diazoalkanes having one to four carbon atoms is the preferred method for formation of the n-alkyl esters. After preparing a solution of the appropriate n-diazoalkane in ether, which is usually accomplished by the guanidine route ["Reagents for Organic Synthesis," Fieser and Fieser, J. Wiley and Sons, N.Y., 1967, Vol. 1, p. 192], about an equivalent of it can be added to a solution of the appropriate carboxylic acid in ether at 0° to 30° C. After several minutes the reaction is usually complete and the product ester, J, wherein $R_2$ is n-alkyl, can be isolated by column chromatography or by simple removal of solvent.

The t-butyl esters can be prepared by the procedure of W. S. Johnson, et. al., Org. Sym. Col. Vol. 4, 261 (1963).

Imide formation is effectively achieved by contacting a carboxylic acid compound of formula E, F, G or H with an alkanoylisocyanate having two to five carbon atoms in the alkanoyl group or benzoylisocyanate which are prepared according to the procedure of A. J. Spiziale, J. Org. Chem., 27, 3742 (1962). The usual procedure calls for contacting a stoichiometric amount of the carboxylic acid compound E, F, G or H, alkanoyl or benzoylisocyanate and a tertiary organic amine base in an inert solvent such as tetrahydrofuran, benzene, dimethoxy ethane or dioxane at temperature of 0° to ambient for 5 minutes to 120 minutes or until the imide formation is essentially complete. The imide product, I, can then be isolated and purified by such common techniques as column chromatography and high pressure liquid chromatography.

When it is desired to make an imide I of carboxylic acid compound E or H, it is necessary to first protect the 9-hydroxyl moiety with a tetrahydropyran-2-yl group as described in U.S. Pat. Nos. 3,932,389 and 3,954,741. This group can then be removed after the alkanoyl or benzoyl isocyanate reaction by contacting the thus formed compound with 65:35 acetic acid/water at about 40° C. usually overnight. In this fashion, the imides I wherein W is an α-hydroxyl group can be made.

In numerous in vivo and in vitro tests, it has been established that the prostamimetic compounds of the present invention exhibit extreme selectivity. Their biological achievement is the diminution of many of the physiological activities of the natural prostaglandins while maintaining activity in one area. The tests which allow such determination of selectivity include among others, a test for effect on isolated smooth muscle from guinea pig uterus, inhibition of histamine-induced bronchospasm in the guinea pig, effect on dog blood pressure, inhibition of cold stress-induced ulceration in the rat, diarrheal effect in the mouse, and inhibition of stimulated gastric acid secretion in rats and dogs.

After comparison to the responses by natural prostaglandins, the physiological responses observed in these tests are useful in determining the utility of the test substance for the treatment of natural and pathological conditions. Based upon such comparison, the determined utility of the prostamimetic compounds of the present invention is the prevention of peptic ulcers. This selective utility is made apparent by the existence of comparable anti-secretory and potent anti-ulcer activity in the prostamimetic compounds of the present invention relative to the natural prostaglandins while exhibiting a diminution in such determined activities as hypotensive activity, bronchodilator activity, smooth muscle activity and diarrhea activity.

The ability to prevent or reduce peptic ulcers by the prostamimetic compounds of the present invention was examined by several methods which are the modified Ghosh and Schild rat anti-secretory model [G. A. Pissidis, et al., Gut, 8, 196 (1967)] and the stress-induced rat ulceration model [W. E. Perkins, et al., Brit. J. Pharmacol, 47, 847 (1973)]. A prime example of the therapeutic importance of these prostamimetic compounds is the efficacy of 9-oxo-14-(benzylthio)-cis-5-ω-hexanorprostenoic acid which caused an inhibition of gastric acid secretion in the above anti-secretory model of approximately 40% that of $PGE_2$ and reduced the incidence of ulceration damage in the above ulceration model by 50% compared to controls ($PGE_2$ is ineffective in this test).

For pharmaceutical formulation and for solid compounding of the prostamimetic compounds of the present invention, the useful pharmacological acceptable salts are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron, are within the scope of this invention.

Pharmacologically acceptable amine cations are those derived from primary, secondary, or tertiary amines. Examples of suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and aliphatic amines containing up to and including about 8 carbon atoms, as well as heterocyclic amines, e.g., piperidine, morpholine, pyrrolidine, piperazine, and loweralkyl derivatives thereof, e.g., 1-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglucamine, N-methylglucosamine, epherdrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium and the like.

The new compounds of this invention can be used in a variety of pharmaceutical preparations which contain the compound or a pharmaceutically acceptable salt thereof, and they may be administered in the same manner as natural prostaglandins by several routes, such as intravenous, oral and intraperitoneal. Although the particular dose, formulation and route of administration are dependent upon each patient's unique condition and the wisdom of his attending physician, the guidelines set forth below for the 11-desoxy-15-thia-16-aryl-ω-tetranorprostaglandin compounds describe their usefulness as anti-ulcer agents. For treatment of peptic ulcer, these drugs including their pharmaceutically acceptable salts are appropriately administered intravenously, intraperitoneally or orally in appropriately compounded or uncompounded forms such as aqueous suspensions or solutions, alcoholic solutions or preferably as capsules or tablets at doses of 0.005 to 0.5 mg/kg/dose with up to 12 doses per day.

To prepare any of the above dosage forms or any of the numerous other forms possible, various reaction-inert diluents, excipients or carriers may be employed. Such substances include, for example, water, ethanol, gelatins, lactose, starches, magnesium stearate, talc, vegetable oils, benzyl alcohols, gums, polyalkylene glycols, petroleum jelly, cholesterol and other known carriers for medicaments. If desired, these pharmaceutical compositions may contain auxiliary substances such as preserving agents, wetting agents, stabilizing agents, or other therapeutic agents such as antibiotics.

The following examples are merely illustrative, and in no way limit the scope of the appended claims. The spectral data were obtained on a Varian T-60 or an A-60 NMR and a Perkin-Elmer Grating Infrared Spectrometer. The infrared data are given in microns and the NMR data are given in δ parts per million using TMS as a standard. Melting points are uncorrected and are in ° Centigrade.

In general, the temperatures of the reactions described in the examples, when unspecified, will be taken to mean ambient or room temperature which varies from 15° to 30° C.

The time requirements of the reactions described in the examples, unless otherwise stated, were determined by monitoring with thin layer chromatography (TLC). The usual TLC system was silica-gel on glass (E. Merck-Silica Gel plates, E. Merck, Dormstadt, W. Germany) with benzene/ether or methanol/chloroform as eluants and vanillin/ethanol or iodine as developers ["Introduction to Chromatography" J. M. Bobbitt, A. E. Schwarting, R. J. Gritter, Van Nostrand-Reinhold, N.Y. 1968]. As a general rule, the reaction in question was deemed essentially complete when the TLC spot representing the critical starting material had disappeared or had quit changing in appearance.

EXAMPLE I

Diethyl(benzylthiomethyl)phosphonate

A mixture of benzyl chloromethyl sulfide (20 g., 0.116 mole), prepared according to the method of Bohme, Fischer and Frank [Ann., 563, 54 (1949)], and triethylphosphite (26.9 g., 0.162 mole) was heated with stirring at 155° C. (bath temperature) for 8 hours under a nitrogen atmosphere. The temperature of the oil bath was then raised to 170° C. and the volatile materials removed by distillation under reduced pressure. The residue was chromatographed on silica by eluting with ethyl acetate/benzene mixtures which gave 21.5 g. of the title compound as a liquid.

NMR (CDCl$_3$) δ ppm: 1.32 (3H, triplet, J = 7Hz), 2.55 (2H, doublet, J = 13Hz), 4.22 (2H, quartet, J = 7Hz), 7.32 (5H, singlet).

EXAMPLE II

Diethyl(benzylsulfinylmethyl)phosphonate

A solution of diethyl (benzylthiomethyl)phosphonate (10 g., 0.036 mole) in 75 ml. of methylene chloride was, with ice-bath cooling, treated with 7.29 g. (0.036 mole) of m-chloroperoxybenzoic acid portionwise. After the addition was complete, the mixture was stirred for 1 hour at ambient temperature, filtered to remove precipitate, and the filtrate concentrated in vacuo. The residue was chromatographed on silica gel by eluting the column with ethyl acetate which gave 5.9 g. of the title compound.

NMR (CDCl$_3$) δ ppm: 1.31 (2H, triplet, J = 7Hz), 4.18 (2H, multiplet), 7.36 (5H, singlet).

Using the procedures of Examples I and II, the following phosphonates can be prepared from the appropriate aryl chloromethyl sulfide.

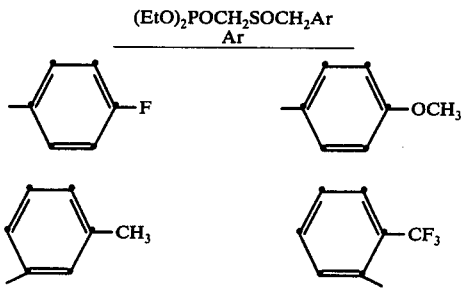

EXAMPLE III

2-[5α-hydroxy-2β-(benzylsulfinylvinylenyl)cyclopent-1α-yl]-acetic acid, γ-lactone 2

Diethyl (benzylsulfinylmethyl) phosphonate, 6.0 g. (0.02 mole) was dissolved in 60 ml. of dimethoxyethane, cooled in an ice-bath and treated with 8.3 ml. of a 2.4M solution (0.02 mole) of n-butyl lithium (ca. 15 minutes). After the addition was complete, stirring was continued for an additional 5 minutes at which time 3.08 g. (0.02 mole) of 2-[2β-formyl-5α-hydroxycyclopent-1α-yl]acetic acid, γ-lactone, 1 [E, J. Corey and B. B. Snider, J. Org. Chem., 39, 256 (1974)] in 15 ml. of dimethoxyethane was added dropwise (1 to 2 minutes) at 0° to 5° C. The mixture was stirred overnight at room temperature and then treated with 1.0 ml. of glacial acetic acid. Filtration of the reaction mixture through celite and evaporation of the filtrate on a rotary evaporator left a residue which was partitioned between ethyl acetate and water. The organic phase was dried with magnesium sulfate, filtered to remove the drying agent and concentrated to give an oil which was chromatographed on silica gel by eluting the column with ethyl acetate. The three fractions obtained consisted of:

(a) 1 g. of crystalline material m.p. 117°-119° C.;
(b) 1.5 g. of oily material; and
(c) 1.4 g. of crystalline material m.p. 99°-104° C.; and were grossly identified as being the geometric isomers of the title compounds.

The physical characteristics of each of these three fractions were as follows:

(a) m.p. 117°-119;20 C.; IR (μ, KBr); 5.67, 8.6, 9.6.
(b) oil, IR (μ, neat); 5.66; 8.62, 9.67.
(c) m.p. 99°-104° C., IR (μ, KBr): 5.65, 8.53, 9.7.

As stated above, the three fractions were geometric isomers of lactone 2. They consist of the cis, trans mixture of the double bond and R, S mixture of the sulfoxide. For the purposes of the synthesis to follow, the combination of all fractions provided equivalent material to any of the geometric isomers,. Therefore, all fractions were used in the subsequent reduction step, Example IV.

By employing the procedure of Example III and substituting the appropriate phosphonate for diethyl(-benzylsulfinylmethyl)phosphonate, the following lactone 2 analogs can be made:

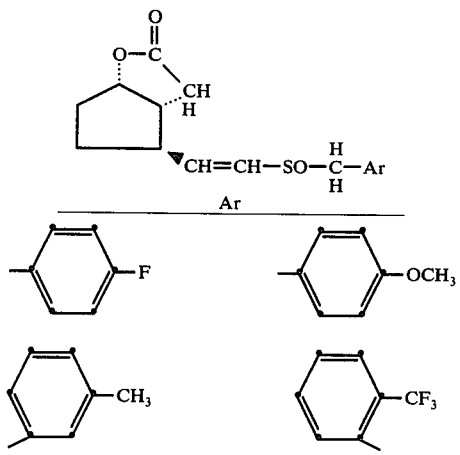

EXAMPLE IV

2-[5α-hydroxy-2β-(benzylthiovinylenyl)cyclopent-1α-yl] acetic acid, γ-lactone, 12

A solution, cooled to 0° C., of 6.5 g. (14.9 mmoles) of benzylthiomethyl triphenyl phosphonium chloride in 40 ml. of tetrahydrofuran is treated with 6.2 ml. of a 2.4M solution of n-butyl lithium in hexane. After stirring for 10 minutes at ambient temperature, to the phosphorane solution is added 2.3 g. (14.9 mmoles) of 2-[2β-formyl-5α-hydroxycyclopent-1α-yl]acetic acid, γ-lactone, 1, in 7 ml. of tetrahydrofuran. The reaction is stirred until substantially complete and the title compound can be isolated by common techniques such as extraction, filtration and chromatography.

By employing the procedure of Example IV and substituting the appropriate phosphonium salt, the following lactone 12 analogs can be made

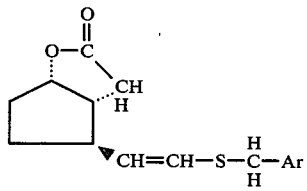

wherein Ar is defined in Example III.

EXAMPLE V

2-[5α-hydroxy-2β-(benzylsulfinylethylenyl)cyclopent-1α-yl]acetic acid, γ-lactone 3 and
2-[5α-hydroxy-2β-(benzylthioethylenyl)cyclopent-1α-yl]acetic acid, γ-lactone 4

A 1 g. (3.0 mmole) mixture of the geometric isomers of 2-[5α-hydroxy-2β-(benzylsulfinylvinylenyl)cyclopent-1α-yl]acetic acid, γ-lactone, 2, was dissolved in 50 ml. of methanol containing 0.5 ml. acetic acid. This solution was then hydrogenated on a Parr hydrogenation apparatus using 1 g. of 10% palladium-on-carbon as catalyst and under a 40 p.s.i. hydrogen atmosphere. After the pressure had dropped to 18 p.s.i., H₂ absorption ceased and the hydrogenation apparatus was stopped. The catalyst was filtered, an additional 2.5 ml. of acetic acid and 1 g. fresh catalyst was added. Again, hydrogenation was carried out in the Parr apparatus under a 40 p.s.i. hydrogen atmosphere. After hydrogen absorption had ceased, the reaction mixture was filtered to remove the catalyst. Evaporation of solvent from the filtrate under reduced pressure left a residue which was chromatographed on silica gel by eluting the column with ethyl acetate. Two fractions were separated and identified as (a) 425 mg. of the title sulfide compound 4 and (b) 500 mg. of the title sulfoxide compound 3.

NMR: sulfide 4 (CDCl3) δ ppm: 3.70 (2H) singlet, 4.90 (1H) multiplet.

IR: (HCCl₃) solution cells, (μ) 8.61.

NMR: sulfoxide 3 (CDCl₃) δ ppm: 4.01 (2H) singlet, 4.91 (1H) multiplet.

IR: (HCCl₃ solution cells), (μ) 9.74, 8.61.

By substituting the other compounds of Examples III for γ-lactone 2 in Example V, the sulfides and sulfoxides having the following structures respectively can be formed. By Substituting the compounds of Example IV for γ-lactone 2 in Example V the sulfide having the structure below can be found.

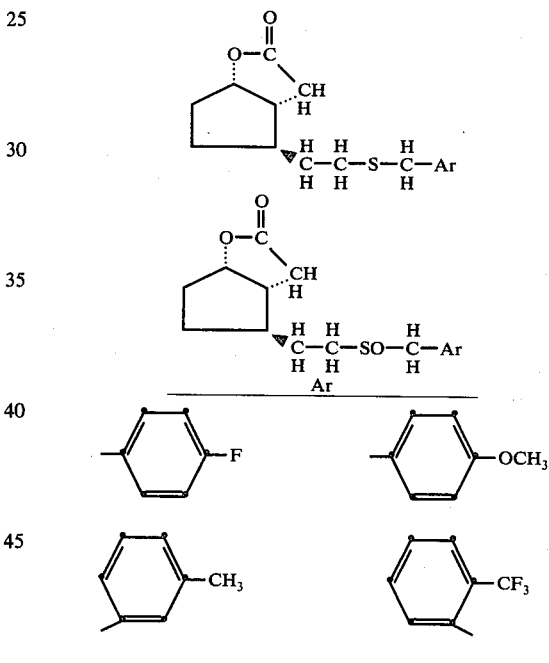

EXAMPLE VI (Nat.)-2-[5α-hydroxy-2β-(benzylthioethylenylcyclopent-1α-yl]-acetaldehyde, γ-hemiacetal 5

A solution of 487 mg. (1.76 mmole) of 2-[5α-hydroxy-2β-benzylthioethylenyl)cyclopent-1α-yl]acetic acid, γ-lactone, 4, in 10 ml. of dry toluene was cooled to −78° C. in a dry nitrogen atmosphere. To this cooled solution was dropwise added 2.2 ml. of a 20% solution of diisobutylaluminum hydride in n-hexane at such a rate so that the internal temperature was never allowed to rise above −65° C. (10 minutes. After an additional 30 minutes of stirring at −78° C., anhydrous methanol was added until gas evolution ceased. The reaction mixture was allowed to warm to ambient temperature, and combined with 150 ml. ether. This organic solution was washed with 50% sodium potassium tartrate solution (2 × 35 ml.) and then with brine (1 × 50 ml.), dried over magnesium sulfate and then filtered to remove the drying agent. After removal of the filtrate solvent in vacuo, the crude product was chromatographed on a silica gel column using ethyl acetate as an eluant to yield 410 mg. of the title γ-hemiacetal 5.

NMR (CDCl₃) δ ppm: 3.68 (2H) singlet; 4.70 (1H) multiplet; 5.57 (1H) multiplet.

Using the same procedure, the other 2-[5α-hydroxy-2β-(arylthioethylenyl)cyclopent-1α-yl]acetic acid, γ-lactones of Example V can be reduced to the corresponding γ-hemiacetals having the structure:

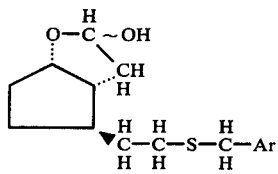

wherein Ar is as previously defined.

EXAMPLE VII

9α-Hydroxy-14-(benzylthio)-cis-5-ω-hexanorprostenoic Acid 6

To a solution of 3.45 g. (7.8 mmoles) of (4-carboxy-n-butyl)triphenylphosphonium bromide in a dry nitrogen atmosphere and in 8 ml. of dry dimethyl sulfoxide was added 7.8 ml. of a 2.0M solution of sodium methylsulfinylmethide in dimethyl sulfoxide. To this red ylide solution was added dropwise a solution of 0.725 g. (2.6 mmole) of (Nat.)-2-[5α-hydroxy-2β-(benzylthioethylenyl)-cyclopent-1α-yl]acetaldehyde, γ-hemiacetal, 5, in 12 ml. dry dimethyl sulfoxide over a period of 20 minutes. After an additional 20 hours stirring at ambient temperature, the reaction mixture was poured onto a mixture of ice water (100 g.), 10% HCl (50 ml.), and ethyl acetate (100 ml.). The acidic aqueous solution was extracted with ethyl acetate (2 × 85 ml.) and the combined organic extracts washed with water (1 × 100 ml.), brine (100 ml.), dried with magnesium sulfate, filtered and the filtrate evaporated in vacuo to a residue. The residue was purified by column chromatography on silica gel using chloroform and ethyl acetate as eluants. After removal of high R_f impurities, 500 mg. of the title compound 6 was collected.

NMR (CDCl₃) δ ppm: 3.7 (2H) singlet, 4.2 (1H) multiplet, 5.45 (2H) multiplet, 7.28 (5H) singlet.

Using the same procedure, the other hemiacetals of Example VI can be converted into 9α-hydroxy prostenoic acids of the following structure:

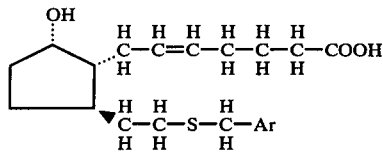

wherein Ar is as previously defined.

EXAMPLE VIII

9-Oxo-14-(benzylthio)-cis-5-ω-hexanorprostenoic Acid 7

To a solution of 0.38 g. (1.04 mmole) of 9α-hydroxy-14-(benzylthio)-cis-5-ω-hexanorprostenoic acid, 6, in 10 ml. reagent grade acetone and which had been cooled to −10° C. and placed under nitrogen, was added dropwise 0.428 ml. of 2.67M Jones' reagent. After 5 minutes at −10° C., 0.5 ml. 2-propanol was added and the reaction mixture was allowed to stir an additional 5 minutes. It was then combined with 50 ml. ethyl acetate, washed with water (3 × 25 ml.), brine (1 × 25 ml.), dried with magnesium sulfate, filtered and the filtrate concentrated to give an oil. Chromatography on silica gel by elution with benzene-ethyl acetate mixtures gave 15 mg. of the title compound.

IR (neat film): 5.75, 6.25

Using the same oxidation procedure, the other compounds of Example VII can be converted into the prostaglandin E compounds of the following structure:

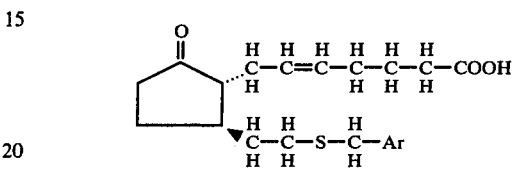

wherein Ar is as previously defined.

EXAMPLE IX

2-Descarboxy-2-(tetrazol-5-yl)-13,14-dihydro-14-(benzylthio)-ω-hexanor PGF₂α 8

To a solution of 7.8 mmoles of (4-tetrazol-5'-yl-n-butyl) triphenylphosphonium bromide in 8 ml. dry dimethyl sulfoxide and in a dry nitrogen atmosphere is added 7.8 ml. of a 2.0M solution of sodium methylsulfinylmethide in dimethyl sulfoxide. To this red ylide solution is added dropwise a solution of 0.725 g. (2.6 mmole) of (Nat.)-2-[5α-hydroxy-2β-(benzylthioethylenyl)-cyclopent-1α-yl]-acetaldehyde, γ-hemiacetal, 5, in 12 ml. dry dimethyl sulfoxide over a period of 20 minutes. After stirring at ambient temperature until the reaction is essentially complete, the reaction mixture is poured onto a 2:1 solution of ice water and 10% hydrochloric acid covered with ethyl acetate. The acidic aqueous solution is extracted with ethyl acetate and the combined organic extracts can be washed with water, brine and dried with magnesium sulfate, filtered and the filtrate evaporated in vacuo to a residue. The residue can be purified by common techniques such as column chromatography and high pressure liquid chromatography. In this way the purified title compound, 8, can be isolated.

Using the same procedure, the other hemiacetals of Example VI can be converted into prostaglandings of the following structure:

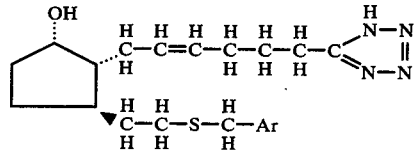

wherein Ar is as previously defined.

EXAMPLE X

2-Descarboxy-2-(tetrazol-5'-yl)-13,14-dihydro-14-(benzylthio)-ω-hexanor PGE₂ 9

To a solution of 1.04 mmole of the 2-descarboxy-2-(tetrazol-5'-yl)-13,14-dihydro-14-(benzylthio)-ω-hexanor PGF₂α, 8, in 10 ml. reagent grade acetone which is cooled to −10° C. and placed under nitrogen, is added dropwise 0.428 ml. of 2.67M Jones' reagent. After 5 minutes at −10° C., 0.5 ml. 2-propanol can be added and the reaction mixture can be allowed to stir an additional 5 minutes. It can then be combined with 50 ml. ethyl acetate, washed with water, dried with magnesium sulfate, filtered and the filtrate concentrated. Purification by any of the common techniques such as column chromatography or high pressure liquid chromatography will allow isolation of the title compound.

Using the same oxidation procedure, the other compounds of Example IX can be converted into the prostaglandin E compounds of the following structure:

wherein Ar is as previously defined.

EXAMPLE XI

9-Oxo-14-(benzylthio)-ω-hexanorprostanoic Acid 10

A solution of 1.0 mmole of 9-oxo-14-(benzylthio)-cis-5-ω-hexanorprostenoic acid, 7, in 50 ml. methanol is hydrogenated on a Parr hydrogenation apparatus using 1 g. of 10% palladium-on-carbon as a catalyst and a hydrogen atmosphere. After the hydrogenation is essentially complete, the catalyst can be filtered from the reaction mixture and the solvent can be removed in vacuo from the resultant filtrate. The residue can then be purified by the common techniques such as column or liquid high pressure chromatography to yield the title compound.

Using the same procedure, the other prostenoic acid and tetrazole compounds of Examples VII, VIII, IX and X can be converted into the corresponding prostanoic acids and tetrazoles.

EXAMPLE XII 9-oxo-14-(benzylthio)-cis-5-ω-hexanor prostenoic, acetic imide

To a solution of 0.072 g. (0.2 mmoles) 9-oxo-14-(benzylthio)-cis-5-ω-hexanorprostenoic acid, 7, in 10 ml. dry tetrahydrofuran can be added 0.2 mmoles of triethylamine followed by 0.2 mmoles acetylisocyanate prepared according to the procedure of A. J. Spiziale, [J. Org. Chem., 27 3742 (1962)] in 5 ml. of dry THF. After stirring for 30 minutes, the solvent can be removed in vacuo and the residue purified according to common techniques such as column chromatography to give the title compound.

In a similar fashion the other carboxylic acid compounds of Examples VII, VIII and XI can be converted into the acetic imides. In addition, by substituting benzoylisocyanate or Alkanoylisocyanates having three to five carbon atoms in the alkanoyl group for acetyl isocyanate in the above procedure, the corresponding benzoic imides and alkanoic imides having two to five carbon atoms in the alkanoic group can be made.

If a 9α-hydroxy prostenimide or prostanimide is to be made, it will be appropriate to prepare the 9-tetrahydropyran-2-yloxy derivative of the 9α-hydroxy prostenoic or prostanoic acids described in Example VII and XI. These derivatives can be used in the above procedure which then can be followed by tetrahydropyranyl cleavage in 65:35 acetic acid:water to give the desired 9α-hydroxy prostenimide or prostanimide compounds.

EXAMPLE XIII

Methyl-9-Oxo-14-(benzylthio)-cis-5-ω-hexanorprostenoate

To a solution of 0.154 mmole of 9-oxo-14-(benzylthio)-cis-5-ω-hexanorprostenoic acid, 7, in 5 ml. of ethyl acetate is added dropwise a solution of diazomethane in ether (ca. 0.3 ml. prepared from N-methyl-N′-nitro-N-nitrosoguanidine according to the procedure found in Fieser and Fieser "Reagents for Organic Synthesis" Volume 1, page 192). After stirring the solution until the reaction is essentially complete, it can be concentrated by removal of solvent in vacuo. The resultant residue can be purified according to common techniques such as column chromatography to produce the title compound.

The other prostenoic and prostanoic acid compounds of Example VII, VIII and XI can be converted into methyl esters by employing them in the above procedure. Other alkyl esters of the prostenoic and prostanoic acids can also be prepared by substituting the appropriate diazoalkane compound for diazomethane in this procedure.

What is claimed is:

1. An optically active compound of the formula and the enantiomer and racemate thereof wherein:
Q is —COOR$_2$;
U is ethylene or cis vinylene W is $\overset{H}{\underset{\cdots OH}{|}}$ or oxygen;
R$_1$ is selected from the group consisting of phenyl and monosubstituted phenyl, said substituent being selected from the group consisting of fluoro, chloro, methyl, methoxy and trifluoromethyl;
R$_2$ is selected from the group consisting of hydrogen and alkyl having one to four carbon atoms;
or a pharmaceutically acceptable alkali metal, alkaline earth metal or ammonium salt of said compound.

2. A compound of claim 1 wherein W is oxygen and R$_1$ is phenyl.

3. A compound of claim 2 wherein Q is —COOH.

4. The compound of claim 1 wherein Q is —COOH, U is cisvinylene, W is oxygen and R$_1$ is phenyl.

* * * * *